United States Patent [19]

Pepper et al.

[11] Patent Number: 5,546,187
[45] Date of Patent: Aug. 13, 1996

[54] SELF-REFERENCING LASER-BASED ULTRASONIC WAVE RECEIVER

[75] Inventors: David M. Pepper; Thomas R. O'Meara, both of Malibu; Phillip V. Mitchell, Simi Valley, all of Calif.

[73] Assignee: Hughes Aircraft Company, Los Angeles, Calif.

[21] Appl. No.: 404,778

[22] Filed: Mar. 15, 1995

[51] Int. Cl.⁶ .................................................. G01B 9/02
[52] U.S. Cl. ........................................ 356/357; 356/349
[58] Field of Search ................................. 356/349, 351, 356/352, 357, 358, 432 T; 73/655, 657

[56] References Cited

U.S. PATENT DOCUMENTS

| | | |
|---|---|---|
| 4,012,946 | 3/1977 | Patsey . |
| 4,112,775 | 9/1978 | Sylvester et al. . |
| 4,180,324 | 12/1979 | Primbsch . |
| 4,275,963 | 6/1981 | Primbsch . |
| 4,480,475 | 11/1984 | Tsao et al. . |
| 4,593,568 | 6/1986 | Telford et al. . |
| 4,619,529 | 10/1986 | Iuchi et al. ............................ 356/358 |
| 4,633,715 | 1/1987 | Monchalin . |
| 4,659,224 | 4/1987 | Monchalin ............................ 356/352 |
| 4,911,537 | 3/1990 | Ewbank ................................ 350/354 |
| 4,966,459 | 10/1990 | Monchalin . |
| 4,991,177 | 2/1991 | Chang et al. ........................... 372/21 |
| 5,080,491 | 1/1992 | Monchalin et al. . |
| 5,113,282 | 5/1992 | O'Meara et al. . |
| 5,121,339 | 6/1992 | Jenuwine et al. . |
| 5,131,748 | 7/1992 | Monchalin et al. .................... 356/349 |
| 5,153,677 | 10/1992 | Keck et al. . |

FOREIGN PATENT DOCUMENTS 3700867   7/1988   Germany .

OTHER PUBLICATIONS

Offside et al., "Common Path Scanning Heterodyne Optical Profilometer for Absolute Phase Measurement", *Applied Physics Letters*, Vol. 55, No. 20 (1989), pp 2,051–2,053.

Scruby et al., *Laser Ultrasonics, Techniques and Applications*, Adam Hilger, New York (1990), pp. 325–350.

Scruby et al., *Laser Ultrasonics, Techniques and Applications*, Adam Hilger, New York (1990), pp. 262–274.

Huang et al., "Dual–Probe Laser Interferometer", *J. Acoust. Soc. Am.*, Vol. 90, No. 3. (Sep. 1991), pp. 1269–1274.

*Primary Examiner*—Samuel A. Turner
*Attorney, Agent, or Firm*—V. D. Duraiswamy; W. K. Denson-Low

[57] ABSTRACT

An optical self-referencing ultrasonic receiver for detecting ultrasonic waves removes wavefront distortions imparted on the optical beams by diffusely reflecting readout surfaces or other sources, compensates for noise induced phase errors on the readout beam, compensates for amplitude noise present on the readout beam, substantially matches the wavefronts of the readout and reference beams, is capable of operating in a heterodyne mode and is self-aligning. In one embodiment, ultrasonic waves are measured by directing a signal beam and a reference beam to a surface of the workpiece so that the signal beam reflects off an area that is being vibrated by the ultrasonic waves, and the reference beam reflects off a different area of the surface. The signal beam gets phase modulated by the ultrasonic wave induced vibrations and also by other noise induced vibrations. The reference beam only gets phase modulated by the noise induced vibrations. The phase modulated signal and reference beams are directed to a wavefront compensator that overlaps the beams, substantially matches their wavefronts and removes wavefront distortions without altering their respective optical phases. The wavefront compensated beams are directed to a coherent detector whose output signal has a phase shift which corresponds to the difference between the optical phase shift on the signal beam (due to ultrasonic wave vibrations and noise vibrations) and the optical phase shift on the reference beam (due to noise vibrations only). Thus, noise induce vibrations common to both beams are canceled out.

36 Claims, 6 Drawing Sheets

SELF-REFERENCING LASER-BASED ULTRASONIC WAVE RECEIVER

BACKGROUND OF THE INVENTION

1. Field of the Invention

This invention relates to ultrasonic receiver systems and more specifically to a laser-based, self-referencing, non-contacting ultrasonic receiver system.

2. Description of the Related Art

Ultrasonic waves are commonly used to probe a variety of materials, particularly for flaw detection. In typical flaw detection systems, the ultrasonic waves are used to probe the workpiece. The waves reflect or scatter from an internal feature or flaw and propagate to a surface of the workpiece, causing the surface to vibrate.

Optical ultrasonic detection techniques, such as those described in C. B. Scruby and L. E. Drain, *Laser Ultrasonics, Techniques and Applications*, Adam Hilger, New York (1990), pages 325–350, are used to remotely detect the ultrasonic waves at the surface of the workpiece. Generally, a laser beam is reflected or scattered from the vibrating surface of the workpiece. The vibrating surface imparts a phase shift to the reflected beam, which is then optically interfered with a reference beam that originates from the same laser source as the reflected beam. The beat frequency between the reflected and reference beams corresponds to the surface motion.

One problem associated with laser detection systems is the presence of extraneous acoustic noise sources which cause additional vibrations at the surface. These additional vibrations are picked up by the reflected laser beam and reduce the signal-to-noise ratio of the system.

Another problem associated with optical systems is low sensitivity. Typically, the surface of the workpiece that is being probed has a diffusely reflecting or scattering quality. Consequently, the reflected beam is highly aberrated and its wavefront is mismatched with respect to the reference beam. Since the optical interference efficiency between the reflected beam and the reference beam depends, in part, upon how well their wavefronts match, the sensitivity of the system is low for diffusely scattering surfaces.

One prior laser based ultrasonic detection system, described in U.S. Pat. No. 5,131,748, entitled "BROADBAND OPTICAL DETECTION OF TRANSIENT MOTION FROM A SCATTERING SURFACE BY TWO-WAVE MIXING IN A PHOTOREFRACTIVE CRYSTAL", issued Jul. 21, 1992 to Jean-Pierre Monchalin, et. al., addresses the wavefront matching problem. In this system, a laser beam is reflected from a vibrating surface of a workpiece, which imparts a phase shift onto the reflected beam that corresponds to the amplitude and frequency of the surface vibration. The reflected beam is caused to optically interfere inside a photorefractive crystal with a "pump" beam that is derived from the same laser as the reflected beam. The two beams write an index of refraction grating inside the crystal that diffracts the pump beam in the propagation direction of the reflected beam. When the diffracted pump beam and the reflected beam exit the crystal, they are overlapping and have substantially matching wavefronts. However, the index grating matches the phases of the diffracted pump beam and the reflected beam.

In interferometry, the sensitivity of the system is maximized-by-biasing the two interfering beams so that they have a $\pi/2$ phase shift between them. Since the phases of the two interfering beams in the Monchalin system are matched, its sensitivity to the small phase perturbations imparted to the reflected beam by the surface vibrations is very small. To overcome this problem, a second frequency shifted pump beam is superimposed onto the first pump beam. The second pump beam is close enough in frequency to the first pump beam to be Bragg matched to the index grating and, therefore, diffracts off this grating. A second index grating is not written by the second pump beam and the reflected beam because the crystal cannot respond fast enough to the moving fringe grating produced between the beams (the frequency shift between the beams results in non-stationary fringes). As a result, the second pump beam only diffracts off the first stationary grating (written by the first pump beam and the reflected beam) and the relative phase between it and the reflected beam is preserved.

Although this technique improves the system's sensitivity, it suffers from many limitations. First, the second pump beam has to be Bragg matched to the stationary grating written by the first pump beam and the reflected beam. As a result one cannot impart the frequency shifts needed to operate the system in a heterodyne mode. Second, although the wavefronts of the reflected beam and the diffracted pump beam are matched, they are matched to the aberrated wavefront of the reflected beam rather than to the clean wavefront of the pump beam. For example, if the reflected beam is highly diverging, the diffracted pump will likewise be highly diverging. This could lower the amount of light available to the optical detectors in the system. Third, if the surface of the workpiece is de-polarizing (either locally or globally), the sensitivity of the detector goes down. In addition, if the workpiece surface contains highly contrasting features (for example, pits, rust, spots, etc.), the two-wave mixing amplification may result in non-uniform "print-through" (due to pump depletion) which will degrade the system performance. Finally, the Monchalin system does not compensate for extraneous acoustic noise sources which could cause additional vibrations at the surface. These additional vibrations would be detected by the Monchalin system and would lower the signal-to-noise ratio.

A profilometer, described in M. J. Offside, M. G. Somekh and C. W. See, "Common Path Scanning Heterodyne Optical Profilometer for Absolute Phase Measurement", *Applied Physics Letters*, Vol. 55, No. 20 (1989), pp. 2,051–2,053, utilizes an interferometric detection system to measure the surface profile of a workpiece. A probe beam is reflected off a small region of a surface of a workpiece and optically combined and interfered with a global reference beam, which is reflected from a different region of the workpiece surface, at a detector. The surface profile is determined by measuring the phase difference between the beams. Phase errors imparted onto the probe beam due to microphonics in the workpiece are compensated by reflecting a compensation beam off a much larger area of the workpiece surface than the probe beam and interfering it with the global reference beam.

Although the Offside system is suitable for surface profiling, it suffers from limitations that make it undesirable as an ultrasonic receiver. First, the system does not compensate for wavefront or polarization distortions imparted onto the reflected beams (from rust spots, absorbing patterns on the surface, cracks, pits, etc.), resulting in reduced sensitivity as explained above. In addition, the system is set up in the form of two Michelson interferometers which require precise alignment of the beams. Any slight misalignment of the beams will lower the system's efficiency.

A dual-probe interferometer for detection of acoustic surface waves is described in Jin Huang and J. D. Achenbach, "Dual-Probe Laser Interferometer", *J. Acoust. Soc. Am.*, Vol. 90, No. 3 (September 1991), pp. 1269–1274. However, this system does not function well with rough surfaces that widely scatter the incident laser beams. In addition, although it compensates for piston noise vibrations, it does not compensate for tilt noise vibrations, dynamic depolarization and dynamic variations in the collected light levels (due to changes in surface absorptions, scattering, etc.).

SUMMARY OF THE INVENTION

In view of the above problems, the present invention provides an optical self-referencing ultrasonic receiver that removes wavefront, depolarization and spatial amplitude distortions imparted to the optical beams by diffusely reflecting surfaces or other sources, compensates for noise induced phase errors on the readout beam, substantially matches the wavefronts of the readout and reference beams, is capable of operating in a heterodyne mode and is self-aligning.

In one embodiment, ultrasonic waves are measured by directing a signal beam and a reference beam to a surface of the workpiece so that the signal beam reflects off a portion of the surface that is being vibrated by the ultrasonic waves, and the reference beam reflects off a different area of the surface. The signal beam is phase modulated by the ultrasonic wave induced vibrations and also by other noise induced vibrations, while the reference beam is substantially phase modulated only by the noise induced vibrations.

The phase modulated signal and reference beams are directed to a photorefractive crystal where they optically interfere with a third independent beam to write photorefractive refractive index gratings inside the crystal. The index gratings diffract the signal and reference beams, substantially match their wavefronts and remove wave front and amplitude distortions without altering their respective optical phases. The diffracted signal and reference beams are substantially overlapping when they exit the crystal and are directed to a detector, which measures the beat frequency between them. The diffracted beams always overlap regardless of changes in one or both of their input angles into the crystal. Thus, the signal and reference beams are self-aligned at the detector.

The detector signal has a phase shift which corresponds to the difference between the optical phase shift on the signal beam (due to ultrasonic wave and noise vibrations) and the optical phase shift on the reference beam (due to noise vibrations only). For "piston motion" noise vibration modes (in which the workpiece vibrates in a direction normal to the surface), the noise induced phase shift is common to both beams and they cancel in the detector output.

In order to compensate for more complex noise vibration modes in which tilt as well as piston motion is present, two reference beams are used. The two reference beams are directed to the surface of the workpiece symmetrically about the signal beam. For a noise induced tilt of the readout surface about the signal beam readout site (or any odd order surface deformation about the signal beam readout site), the signal beam is unaffected (as long as the signal beam readout site is at the center of rotation). However, the reference beams are displaced by equal amounts in opposite directions. When the three beams are optically interfered, the phasor sum of the two reference beams are in phase with the signal beam (as long as the tilt-induced displacements are less than $\lambda/4$), thereby avoiding the effects of surface tilt on the reference beams. Further, since any tilt can be expressed as a tilt about the signal beam readout site plus a piston motion, all small angle tilts that generate displacements of less than $\lambda/4$ will be compensated.

These and other features and advantages of the invention will be apparent to those skilled in the art from the following detailed description of preferred embodiments, taken together with the accompanying drawings, in which:

DETAILED DESCRIPTION OF THE INVENTION

Figure 1:
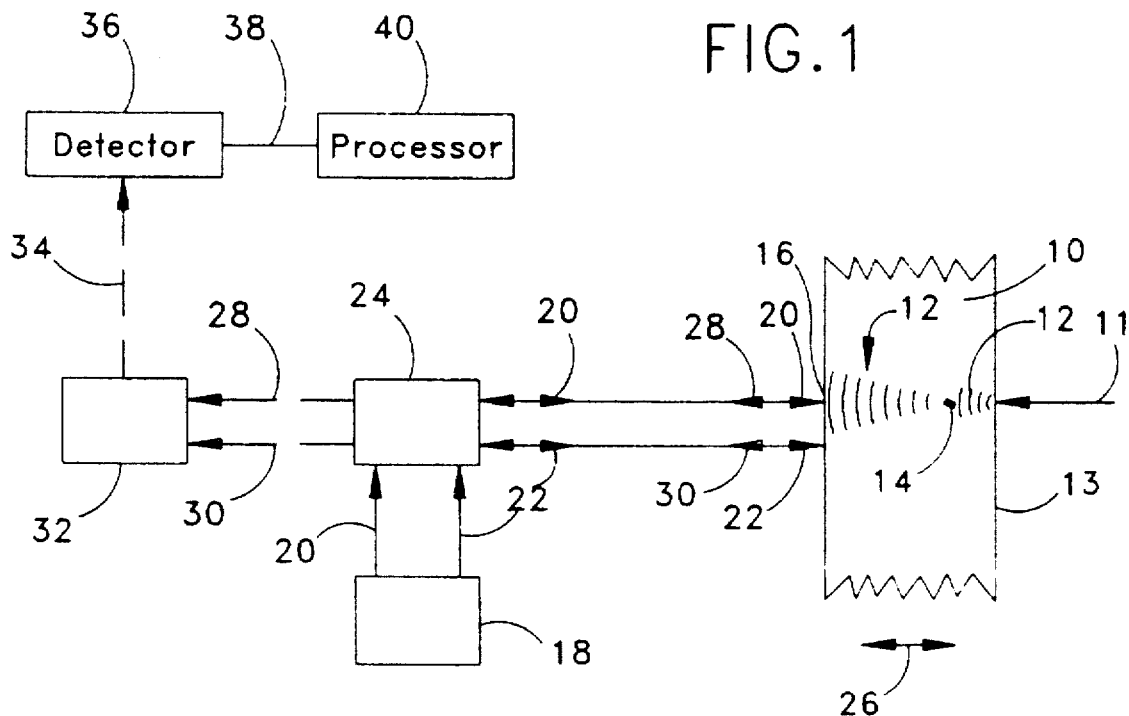
FIG. 1 is a block diagram illustrating the basic principles of the invention.

FIG. 1 illustrates the basic principles of the invention. It is assumed that an ultrasonic wave is used to probe a solid workpiece 10. Such an ultrasonic wave 12 can be generated in the workpiece with a laser beam 11 directed to one side of the workpiece 10. The beam 11 generates ultrasonic waves through either thermoelastic effects or through ablation of material from the surface 13 of the workpiece 10. For an overview of laser techniques used to generate ultrasonic waves, see C. B. Scruby and L. E. Drain, *Laser Ultrasonics, Techniques and Applications*, Adam Hilger, New York (1990), pages 262–274. A portion of the ultrasonic wave 12 scatters or reflects from an internal feature 14, such as a weld or crack, and propagates to the readout surface 16, causing a vibration at the surface 16.

An optical beam generator 18 generates a signal beam 20 and a reference beam 22 having a predetermined mutual frequency relationship. A beam director 24 directs the beams 20 and 22 to the readout surface 16. In some applications (such as weld inspection) the location of the internal feature 14 is known and the signal beam 20 is preferably directed to an area on the readout surface 16 that is directly opposite the internal feature 14. The reference beam 22 is preferably directed to an area on the readout surface 16 that is minimally vibrated by the ultrasonic waves 12.

Upon reflection from the readout surface 16, the signal beam 20, but not the reference beam 22, is phase modulated by the vibrations induced on the readout surface 16 by ultrasonic waves 12. Any noise-induced piston movement 26 of the workpiece will phase modulate both the signal and reference beams. The reflected signal beam 28 and reference beam 30 pass back through the beam director 24, which directs them to a wavefront compensator 32.

The wavefront compensator 32 removes any wavefront polarization or amplitude distortions imparted on the reflected signal and reference beams by the readout surface 16. In addition, the compensator 32 overlaps and matches the wavefronts of the reflected signal beam 28 and reference beam 30. The overlapped and wavefront compensated beams 34 are directed to a coherent detector 36, where they optically interfere and generate a beat frequency, whose output signal is phase shifted by an amount that corresponds to the difference between the optical phase shift on the signal beam 20 and the optical phase shift on the reference beam 22. The largest components of surface noise vibration are typically piston motions. Since the phase shifts caused by noise induced piston motions 26 are common to both beams, they cancel in the detector 36 output. The detector output signal is transmitted by a signal cable 38 to a processor 40, which processes the output signal to obtain information about the ultrasonic waves 12 (and hence about the feature 14 which scattered or reflected them).

Figure 2:
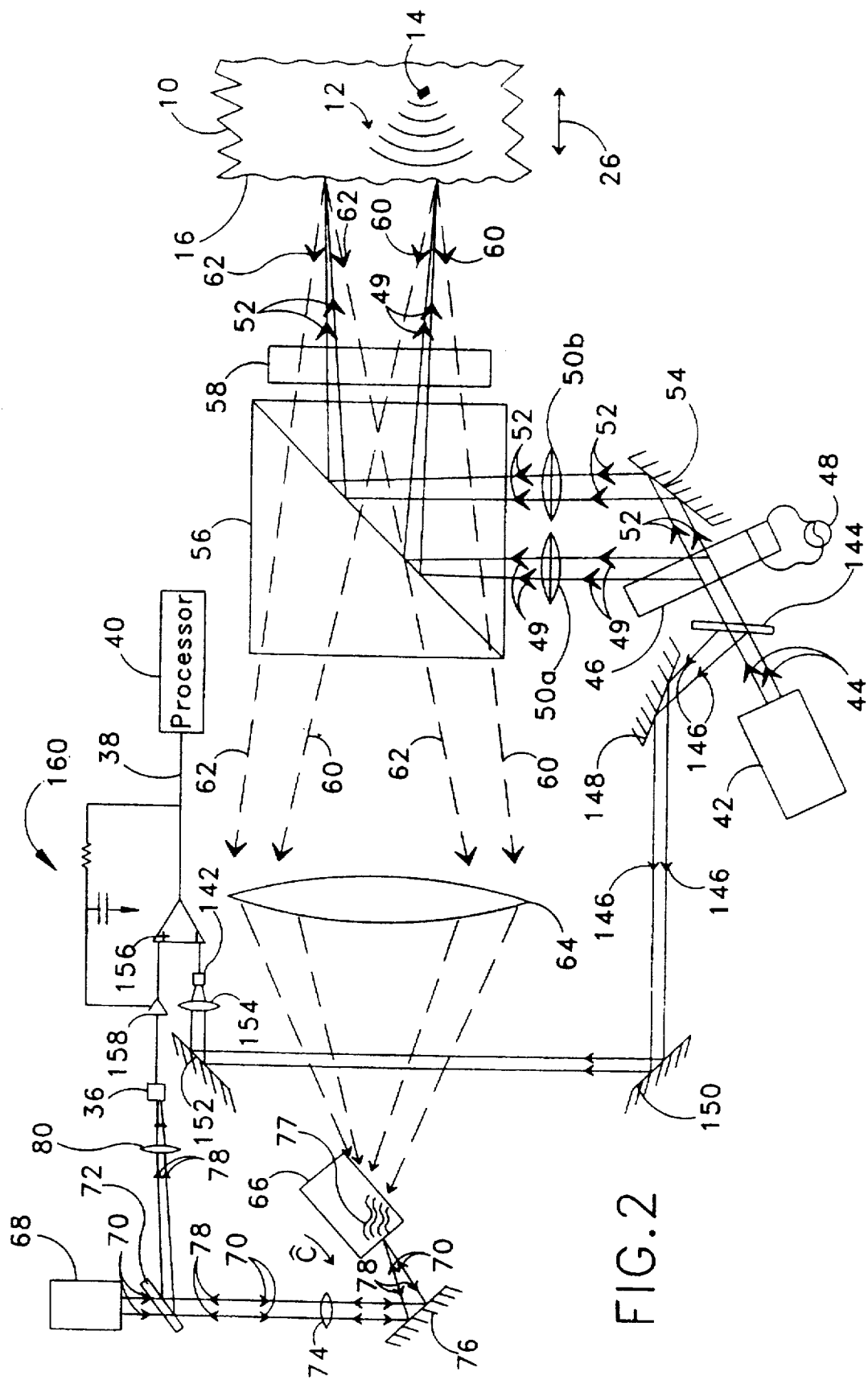
FIG. 2 is a schematic diagram of a two beam self-referencing laser ultrasonic receiver.

FIG. 2 illustrates a preferred embodiment of a two-beam ultrasonic detection system that compensates for noise induced piston motions 26. A laser 42, preferably a diode-pumped, continuous-wave, doubled-YAG laser operating at a wavelength of 532 nm, is used to generate an optical beam 44 that is preferably vertically polarized (normal to the plane of the page). The beam 44 is passed through a Bragg cell 46 that is driven by an AC voltage source 48 to generate an acoustic wave (not shown) in the cell 46 with a frequency of preferably between 20 and 100 MHz. The Bragg cell 46 is oriented with respect to the beam 44 so that the beam hits the cell at the Bragg angle for the acoustic wave. The acoustic wave in the Bragg cell diffracts a portion 49 of the beam 44 to focusing lens 50a. The diffracted beam portion 49 is used as the signal beam and is shifted in frequency with respect to beam 44 by an amount that corresponds to the acoustic wave frequency in the Bragg cell 46. The portion of beam 44 that is not diffracted by the acoustic wave passes through the cell 46 and is used as the reference beam 52, which is directed to focusing lens 50b by mirror 54.

A polarizing beamsplitter 56 reflects the vertically polarized signal and reference beams to a quarter-wave plate 58, which converts their polarizations to circular polarizations. The circularly polarized signal beam 49 and reference beam 52 are directed to the readout surface 16 of the workpiece 10. As explained above, the signal beam 49 is preferably directed to an area on the readout surface 16 that is directly opposite the internal feature 14 that is being probed, and the reference beam 52 is directed to an area that is not being significantly vibrated by the ultrasonic waves 12 propagating from the internal feature 14. The ultrasonic waves 12 are initially established in the workpiece in the same way illustrated in FIG. 1. The focal length of lens 50 is preferably chosen so that the diameter of the signal 48 and reference 52 beams at the readout surface 16 is comparable or less than the uniform part of the acoustically induced surface displacement (typically 1 mm or less).

Upon reflection from the readout surface 16, the signal beam 49, but not the reference beam 52, is phase modulated by the vibrations induced on the readout surface 16 by the ultrasonic wave 12. Any noise induced piston movement 26 of the workpiece will impart a substantially equal phase modulation on both the signal and reference beams. The readout surface 16 is assumed to be smooth enough so that the reflected signal beam 60 and reflected reference beam 62 substantially maintain their circular polarizations. The reflected signal beam 60 and reflected reference beam 62 pass back through the quarter-wave plate 58, which converts their polarizations from circular to horizontal. The reflected beams 60 and 62 pass through the polarizing beamsplitter 56 because they are horizontally polarized.

A focusing lens 64 captures the reflected beams 60 and 62 and directs them into a photorefractive crystal 66 that is used as a double-pumped phase conjugate mirror (DPCM). For some examples of laser beam cleanup using DPCMs, see U.S. Pat. No. 4,991,177, entitled "LASER BEAM CLEAN-UP USING MUTUALLY PUMPED PHASE CONJUGATION", issued Feb. 5, 1991 to T. Y. Chang, et al., and U.S. Pat. No. 4,911,537, entitled "BIRD-WING PHASE CONJUGATION USING MUTUALLY INCOHERENT LASER BEAMS", issued Mar. 27, 1990 to M. D. Ewbank. The photorefractive crystal 66 is preferably $BaTiO_3$, but it could also be $Ba_{2-x}Sr_xK_{1-y}Na_yNb_5O_{15}$, $KNbO_3$, $Sr_{1-x}Ba_xNb_2O_6$ or any other photorefractive crystal. In addition, the DPCM implementation is not limited to a photorefractive crystal. Other types of nonlinear materials could be used in place of a photorefractive crystal.

The signal and reference beams are preferably directed into an a-face of the photorefractive crystal 66. A second independent laser 68 is used to generate a horizontally polarized, plane-wave, compensator reference beam 70 with a uniform intensity profile, which passes through a beamsplitter 72 and is focused and directed to the +c-face of the crystal 66 by a lens 74 and a mirror 76. The compensator reference beam 70 and the reflected signal and reference beams 60 and 62 write mutual photorefractive index gratings 77 in the photorefractive crystal 66 through the photorefractive effect. The signal and reference beams each diffract off the mutual gratings 77 to form two phase conjugates of the compensator reference beam. Since the diffracted signal and reference beams 78 are phase conjugates of the compensator reference beam 70, their wavefronts are matched to the clean wavefront of the compensator reference beam 70. However, the phase modulations imparted by the vibrating readout surface 16 are not affected. In addition, the diffracted signal and reference beams 78 overlap and propagate back towards the second laser along the same path as the compensator reference beam. This propagation path is unaffected by changes in the angle at which the reflected signal and reference beams 60 and 62 enter the a-face of the crystal 66. Therefore, the diffracted signal and reference beams 78 are auto-aligned. In summary, the DPCM generates two overlapped, wavefront matched, distortion free, phase modulated signal and reference beams 78 as a result of diffraction from the mutual index gratings formed in the crystal 66.

Most DPCMs function best when the optical beams generated by lasers 68 and 42 are mutually incoherent. Therefore, in the preferred embodiment two separate and independent lasers are used. However, the frequency difference between the two laser 68 and 42 outputs need only be small. Explicitly, it only has to exceed the inverse of the grating formation time in the photorefractive crystal 66. As a result, a single laser can be substituted for laser 68 and 42 if beam 70 is offset in frequency by a Bragg cell, or if beam 70 possesses a coherence length that is short with respect to the differences in the distances traversed by all the beams that impinge on the DPCM.

The diffracted signal and reference beams 78 retrace the path of the compensator reference beam 70 and are directed by beamsplitter 72 to a focusing lens 80, which focuses them onto a coherent detector 36, where they optically interfere. Since the signal beam 49 was frequency shifted by the Bragg cell 46, the coherent detector 36 operates in a heterodyne mode and its output signal is at the Bragg cell driving frequency with a phase shift that corresponds to the difference between the optical phase shift produced by the vibrating readout surface 16 underlying the signal beam 49 and that of the reference beam 52. Since the phase shifts caused by noise induced piston motions 26 are common to both beams, they cancel in the detector 36 output.

In the case where lasers 42 and 68 are separate independent lasers with a wavelength difference of 1% or more, a dichroic beamsplitter is preferably used as beamsplitter 72. The dichroic beamsplitter 72 is chosen so that it transmits substantially all of beam 70 and reflects substantially all of the diffracted signal and reference beams 78 towards focusing lens 80. This increases the amount of signal available for detection because a conventional beamsplitter would only reflect approximately half of the diffracted signal and reference beams 78.

Another decoupling technique by which to couple out a maximum amount of light with lasers that are closely spaced in wavelength is to use a polarization rotation approach. Under this approach, beamsplitter 72 is replaced with a polarizing beamsplitter, a 45 degree non-reciprocal polarization rotator and a 45 degree reciprocal polarization rotator, with the two polarization rotators positioned between the polarizing beamsplitter and the photorefractive crystal 66. The polarization of laser 68 is set so that 100 percent of the output beam 70 propagates through the polarizing beamspliter and towards the crystal 66. The polarization of beam 70 will be maintained after it propagates through both of the polarization rotators. However, the polarization of beam 78, which propagates in a direction opposite to that of beam 70, will be rotated by 90 degrees after passage through the two polarization rotators. As a result, substantially all of beam 78 is coupled out of the system and directed to lens 80 by the polarizing beamsplitter. The polarization technique described above for decoupling two counter-propagating optical beams is also described in U.S. Pat. No. 5,113,282, entitled "DUAL LIGHT VALVE SYSTEM WITH SELECTIVE DECOUPLING OF LIGHT VALVES", issued May 12, 1992 to Tom O'Meara and David M. Pepper and assigned to Hughes Aircraft Company, the assignee of the present invention.

Laser 42 (as well as most lasers) may generate low level noise modulations in the frequency range of the acoustic signals. Although these are usually weak noise sources, they have significant signal jamming potential because the modulations produced by acoustically induced surface motions are also quite small. To compensate for these low level laser-induced noise modulations, a second detector 142 is used. Detector 142 is a direct detector that is driven with the same laser 42 which produced the surface probe beams. Beamsplitter 144 splits off a portion 146 (a detector reference beam) of beam 44, which is directed and focused onto detector 149 by mirrors 148, 150 and 152 and lens 154. Any laser-induced amplitude noise modulation is thus present in the outputs of both detectors (36 and 142). If the laser input powers to detectors 36 and 142 are matched, then differential amplifier 156 will cancel the laser-induced amplitude noise modulation (typically low frequency modulation) as well as higher frequency additive noise components while leaving the high-frequency acoustic wave induced signal intact.

Since the workpiece surface 16 reflectivity and its effect on the polarization of the reflected probe beams will generally be unknown and time varying, the input to detector 36 will also be time varying. To accommodate this variation, an Automatic Gain Control (AGC) circuit 160 is used which balances the amplitudes of the low frequency components in the outputs of detectors 36 and 142. The AGC circuit comprises an AGC amplifier 158 and an AGC feedback loop 160. The AGC circuit must have a response speed that is adequate to track the rate of change in workpiece surface 16 reflectivity. The differential amplifier 156 and the AGC amplifier 158 must have a bandwidth that is large enough to accommodate a frequency that is equal to the highest acoustic frequency to be processed plus the frequency of the Bragg cell driver 48. Under these conditions, the high frequency components of the acoustic signal are extracted as a substantially noise-free (laser-induced) output.

The differential amplifier 156 output signal is transmitted by a signal cable 38 to a processor 40, which processes the output signal to obtain information about the ultrasonic waves 12 (and hence about the feature 14 which scattered or reflected them). The AGC circuit also serves to hold the input to processor 40 constant in the presence of workpiece surface reflectivity changes or changes in the effective DPCM signal output.

Figure 3:
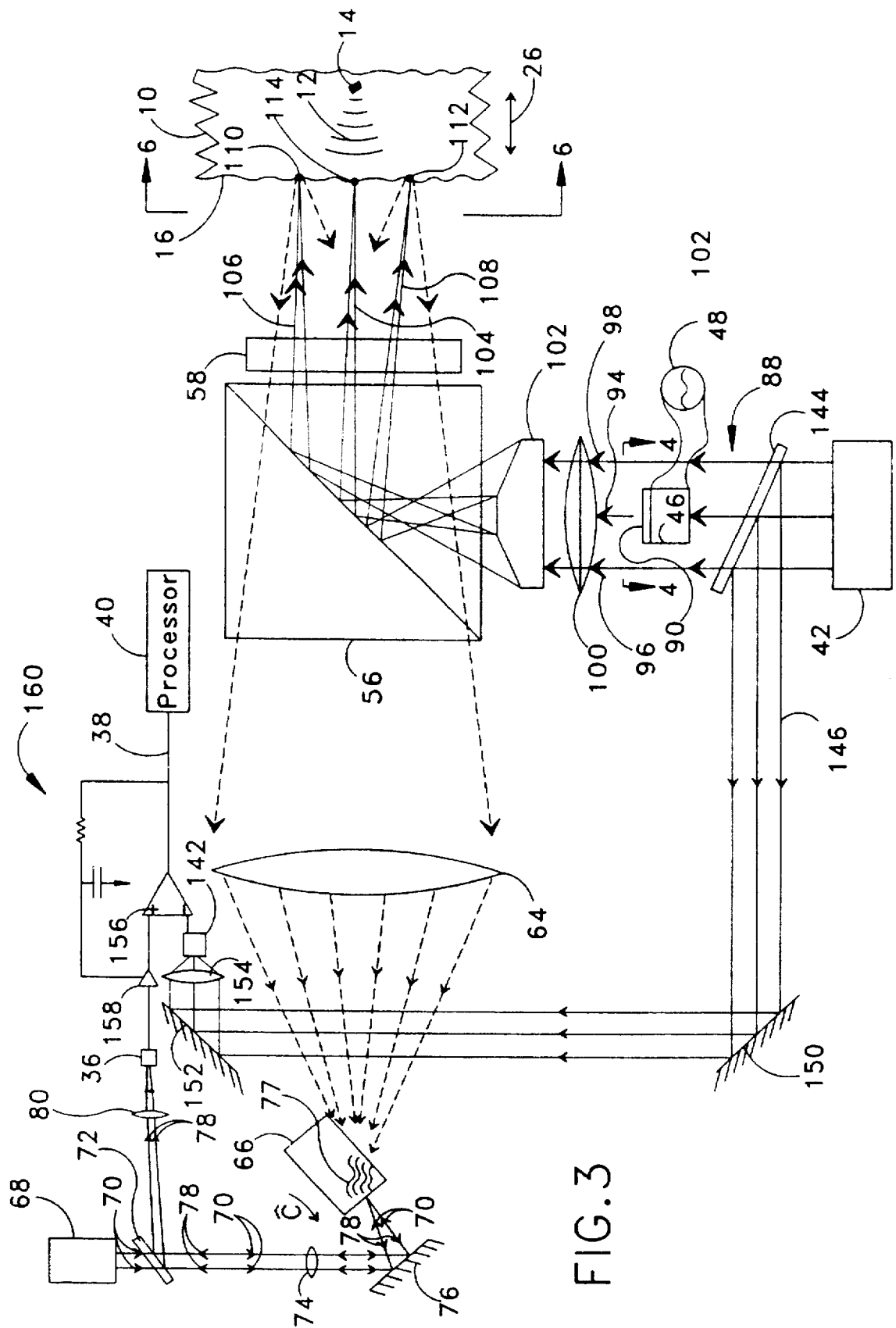
FIG. 3 is a schematic diagram of a three beam self-referencing laser ultrasonic receiver.

The two-beam embodiment described above removes noise induced phase modulations arising from piston movement of the workpiece in the absence of tilt. However, there may be instances when vibration induced noise may cause tilting of the readout surface. If the readout surface tilts, a differential phase shift will arise between the signal and reference beams that can destroy their predetermined mutual phase relationship (because the tilt-induced phase shift imparted to the signal beam is different from that imparted to the reference beam). Although a tilt in general may be represented by a tilt about the signal beam readout site plus a piston displacement, we refer to a tilt component as one centered on the readout site. FIG. 3 illustrates a three-beam embodiment designed to compensate for both piston movement and surface tilting about the signal beam readout site. The theory of operation of the three-beam system is generally similar to the two beam system, except that two reference beams are used instead of the one reference beam used in the two beam system.

Figure 4:
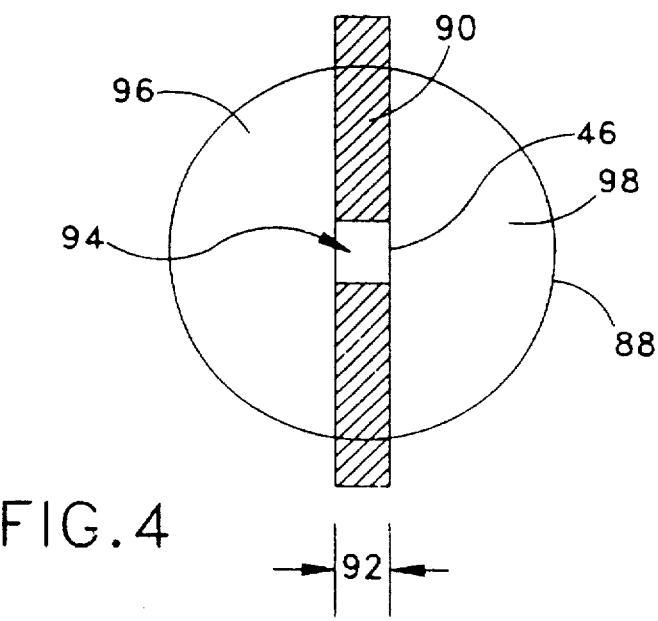
FIG. 4 is a plan view taken along the line 4—4 of FIG. 3.

The three beams are generated by directing an expanded vertically polarized beam 88 from a laser 42 to a Bragg cell 46 that is similar to the Bragg cell used in the two-beam system, except that it is rotated by 90 degrees with respect to the orientation shown in FIG. 2. The transducer (not shown) in the Bragg cell 46 generates a sound wave which propagates normal to the plane of the figure. The beam 88 is expanded so that, in the horizontal direction, only a portion enters the Bragg cell 46. The tilt of the Bragg cell 46 is adjusted so that the beam portion that enters the cell is at the Bragg angle for the acoustic wave in the cell. A rectangular mask 90 with a center aperture is placed at the output end of the Bragg cell 46. The mask 90, which is shown in greater detail in FIG. 4, is preferably made from a light absorbing material and is placed directly in front of the Bragg cell 46. The width 92 of the Bragg cell 46 and mask 90 is preferably equal to 2/10 of the diameter used for the beam 88. Since the diameter of the beam 88 is greater than the width 92 of the Bragg cell 46, only a portion of the beam 88 passes through the cell 46. The mask 90 extends over the top and bottom portions of the cell 46 at the output end so that only a small center portion 94 of the beam 88 passes through the cell and is frequency modulated, preferably by a modulation frequency between 20 and 100 MHz. This center portion 94 becomes the signal beam, and the frequency shift imparted by the Bragg cell 46 allows the system to operate in a heterodyne mode. The left 96 and right 98 portions of the beam 88 that do not pass through the Bragg cell 46 becomes the two reference beams.

Figure 5:
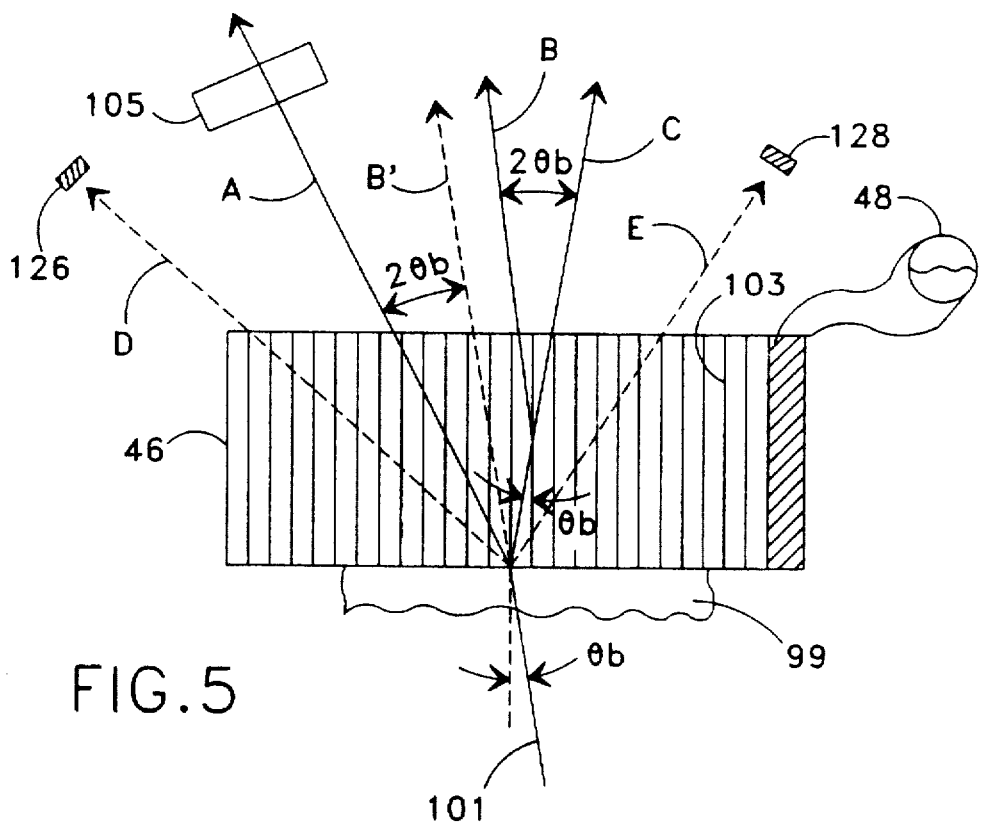
FIG. 5 is a schematic diagram of an alternative beam divider for the embodiment of FIG. 3.

An alternative way to split the main beam into a frequency shifted signal beam and two reference beams is illustrated in FIG. 5. A sinusoidal diffraction grating 99 is formed on the input surface of the Bragg cell 46. The cell 46 is oriented so that a main beam 101 strikes the grating 99 at the Bragg angle $\theta_b$ for an acoustic wave 103 inside the cell 46. The amplitude of grating 99 is preferably large enough to diffract substantially all of the energy out of the zero-order beam B'. The ± first order beams A and C become the reference beams. The diffraction grating period is chosen so that the diffraction angles for the A and C beams (with respect to the zero order beam B') are equal to twice the Bragg angle $\theta_b$. In this way, the A beam is mismatched to the Bragg angle of the acoustic wave 103 and passes through the cell 46 undiffracted. However, the C beam is matched to the Bragg angle of the wave 103 and a substantial portion is diffracted as beam B, which is frequency shifted and will become the signal beam. Beams A and C are intrinsically unequal in magnitude, but this can be rectified by the addition of a partially absorbing plate 105 in the A beam path after the Bragg cell 46. The higher diffracted orders (D and E) are blocked by beam blocks 126 and 128.

Referring back to FIG. 3, a lens 100 and axicon 102 shape and focus beams 94, 96 and 98 into a signal beam 104 and two reference beams 106 and 108, respectively, which are reflected and directed to the readout surface 16 by the polarizing beamsplitter 56 as a result of their vertical polarizations. Before reaching the readout surface, the beams' polarization is converted from vertical to circular by the quarter-wave plate 58. As in the two beam system, the signal beam 104 is preferably directed to an area on the readout surface 16 that is directly opposite the internal feature 14 that is being probed. The positioning of the reference beams 106 and 108 at the readout surface 16 depends upon the nature of the ultrasonic waves 12, and will be explained below.

Figure 6:
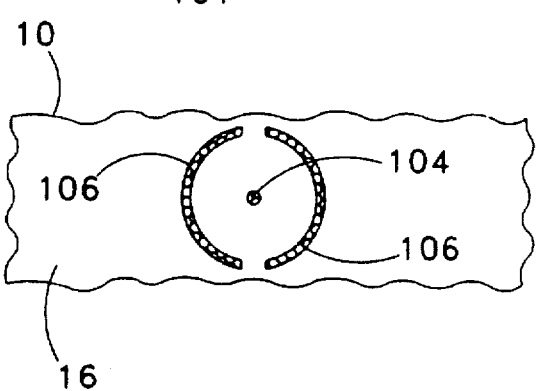
FIG. 6 is an elevation view taken along the line 6—6 of FIG. 3.

The signal and reference beam shapes at the readout surface 16 are controlled by the shape of the mask 90 and by the lens 100 and axicon 102. In the preferred embodiment, a circularly shaped signal beam 104 and symmetric half-ring-shaped reference beams 106 and 108 are used, as illustrated in FIG. 6. The diameter of the signal beam 104 and the thickness of the half-rings 106 and 108 are preferably smaller than the spatial period of the noise induced vibrations. The half-ring-shaped reference beams are preferable because they sample over a larger area of the readout surface. If small circular reference beams were used, a reflection from a bad area (rust, pit, hole, etc.) on the readout surface would adversely affect the measurement. With the half ring-shaped reference beams, a portion of the "ring" could hit a bad area on the readout surface without adversely affecting the overall reflection of the beam from the surface.

With respect to the reference beam positions on the readout surface 16, it is preferable to position them at symmetric positions 110 and 112 with respect to the signal beam 104 and spaced far enough away from the signal beam so that the vibrations generated by ultrasonic wave 12 are not present or are significantly weaker than the ultrasonic wave generated vibrations at the signal beam site 114. If these vibrations are not much weaker at the reference beam sites than at the signal beam site, then the ultrasonic wave induced phase shifts will be present in all three beams and will cancel in the coherent detector 36. However, even if the vibrations are present along the entire readout surface area 16, it is still possible to avoid this problem by an appropriate positioning of the reference beams 106 and 108. Their positioning will depend upon whether the ultrasonic waves 12 are short, broad band pulses or high frequency continuous waves.

For short ultrasonic pulses, the reference beams 106 and 108 are preferably symmetrically positioned about the signal beam 104 and spaced from the signal beam so that the ultrasonic waves 12 arrive at the reference sites 110 and 112 with a delay (with respect to their arrival at the signal beam site 114) that is sufficiently long to allow the coherent detector 36 to read the ultrasonic wave signals from the three beams as non-overlapping pulses. Since the ultrasonic wave induced phase shifts are not present on the signal and reference beams at the same time, they do not cancel at the coherent detector 36.

For continuous ultrasonic waves for which the approximate location of the internal feature 14 is known, the reference beams 106 and 108 should preferably be symmetrically positioned about the signal beam 104 and spaced from the signal beam so that the ultrasonic wave 12 arrives at the reference sites 110 and 112 180 degrees out of phase with respect to the ultrasonic waves at the signal beam site 114. In this way, the difference operation at the coherent detector 36 causes a constructive interference that enhances the combined ultrasonic wave signals over that produced by the signal beam 104 alone.

Figure 7:
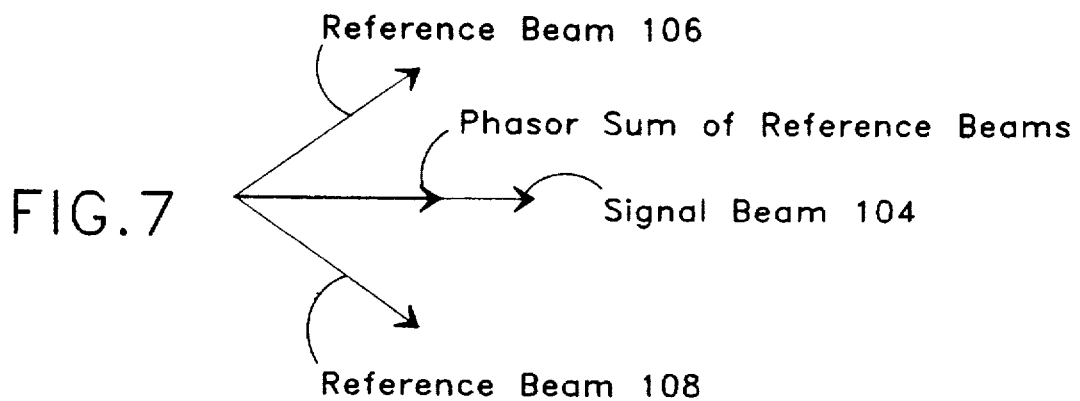
FIG. 7 is a phase diagram illustrating the phase relationship between a signal beam and two reference beams with the embodiment of FIG. 3.

In all cases, the reference beam sites 110 and 112 are preferably symmetrically positioned with respect to the signal beam site 114. This allows the system to compensate for tilting of the workpiece 10 about the signal beam site 114. When such tilting occurs, the reference beam sites 110 and 112 experience equal and opposite displacements with respect to the signal beam site 114. The reflected, phase modulated, wavefront compensated reference beams 116 superimpose at the coherent detector 36 as a phasor sum, as illustrated in the phase diagram of FIG. 7. For differential noise induced phase shifts between the two reference beams of less than 90 degrees, their phasor sum lies in phase with the signal beam. As the displacement of the reference sites 110 and 112 vary with time the magnitude of the phase noise at these sites changes, but the noise still remains in phase with the signal beam site 114. As a result, the predetermined mutual phase relationship between the signal beam and the "effective" reference beam (the sum of the two individual reference beams) is maintained at the DPCM and at the detector.

Figure 8:
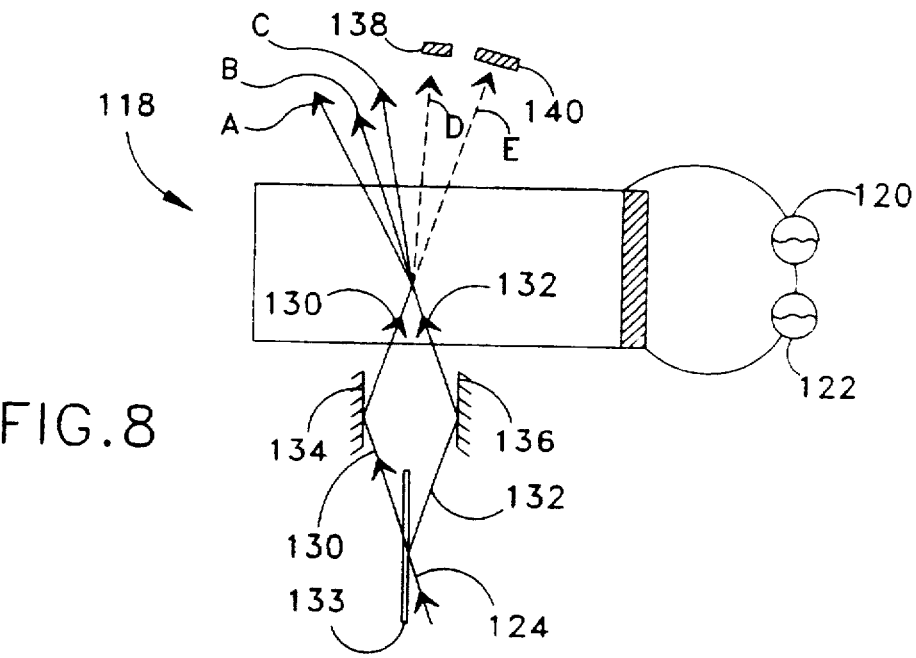
FIG. 8 is a schematic diagram illustrating a beam divider embodiment for a three frequency, three-beam system.

In extreme noise vibration inducing environments in which the differential phase shifts between the reference beams could exceed 90 degrees, a frequency "tagging" scheme is preferably used. Rather than shifting the frequency of only the signal beam at the Bragg cell, the frequency of at least one of the reference beams is also shifted. In order to accomplish this, Bragg cell 46 in FIG. 3 is preferably replaced with the Bragg cell illustrated in FIG. 8. This Bragg cell 118 is driven by two AC voltage sources 120 and 122 to generate two sets of acoustic waves (not shown) at two separate frequencies, for example 20 and 30 MHz. The main beam 124 from the laser is split into beams 130 and 132 by beamsplitter 133. Beams 130 and 132 are reflected into the Bragg cell 118 by mirrors 134 and 136 at incidence angles that satisfy Bragg matching for a frequency that is intermediate with respect to the two Bragg cell 118 driving frequencies (25 MHz for driving frequencies 20 and 30 MHz). The undiffracted portion of beam 132 is not frequency shifted, and is used as signal beam B. The diffracted components D and E are not used and are preferably blocked by beam blocks 138 and 140. Beam 134 is diffracted by each set of acoustic waves. The first diffracted portion is frequency shifted by an amount that corresponds to the first acoustic wave frequency in the cell; this portion is used as reference beam A. The second diffracted portion is frequency shifted by an amount that corresponds to the second acoustic wave frequency in the cell, and is used as reference beam C.

With the exception of the Bragg cell substitution described above, the optical portion of the system remains the same as that illustrated in FIG. 3. After reflection from the readout surface 16, the signal and reference beams at the three separate frequencies are wavefront compensated by the DPCM 66 and directed to the coherent detector 36, which produces three separate sets of difference frequency signal outputs (S1, S2 and S3). S1 has a phase shift ($\theta_C - \theta_A$) which corresponds to the difference between the optical phase shifts imparted to reference beams C and A (in FIG. 8) by the readout surface. Using similar notation, S2's phase shift is ($\theta_A - \theta_B$) and S3's phase shift is ($\theta_C - \theta_B$). The signals S2 and S3 are extracted by filtering and are sent to processor 40 via signal cable 38. As an example, with no shift on signal beam B, 30 MHz shift on reference beam C and 20 MHz shift on reference beam A, S2 is at 20 MHz and S3 is at 30 MHz. An up-converting mixer (not shown) in the processor 40 produces a new signal S4 at 50 MHz with a phase shift that corresponds to the phase shift of S3 plus the phase shift of S2 ($-2\theta_B + \theta_A + \theta_C$). With signal S4, the differential phase shifts of reference beams A and C produced by tilting of the surface are canceled, regardless of their magnitudes. This condition is true for any odd order surface deformation in which $\theta_A = -\theta_C$. For noise induced piston surface motion, the three phase components $\theta_A$, $\theta_B$ and $\theta_C$ cancel as in the two frequency system described above. If only signal beam B includes an ultrasonic wave induced motion component, it remains as an uncontaminated source as in the two frequency system.

In the example given above (with Bragg cell driving frequencies of 20 and 30 MHz), filter separation of the sidebands on the 30 and 50 MHz signals cannot be accomplished for acoustic signal bandwidths that are appreciably larger than 7 MHz. Doubling the Bragg cell driving frequencies (to 40 and 60 MHz) would allow filter separation of the sidebands for acoustic signal bandwidths of up to 14 MHz. 40 and 60 MHz driving frequencies are well within the range of standard Bragg cell drivers.

Figure 9:
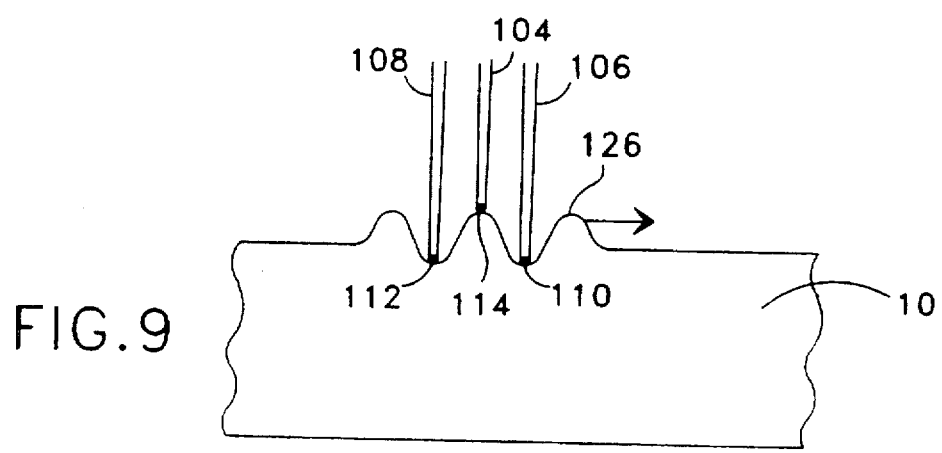
FIG. 9 is a side view of a surface wave propagating along a readout surface of a workpiece and of the signal and reference beams used to measure the surface wave.

The above systems have been described in the context of detecting ultrasonic compression waves that have propagated through a solid workpiece. However, the two and three beam systems may also be used to detect continuous, high frequency surface waves, as well as transient surface wave bursts. For example, FIG. 9 illustrates how the three beam system would measure a continuous surface wave 126 propagating from left to right across the readout surface of workpiece 10. To properly detect the surface wave, the three beams are preferably focused to diameters that are less than one-quarter of the surface wave 126 wavelength at the readout sites 112, 114 and 110. In addition, the readout sites are preferably spaced by a distance equal to one-half the surface wave wavelength, so that the surface wave displacements at the signal beam site 114 and the reference beam sites 112 and 110 are 180 degrees out of phase. In this way the differencing operation at the coherent detector 36 causes a constructive interference that enhances the combined surface wave signals over that produced by the signal beam 104 alone. Noise induced surface vibrations that are common to the signal beam 104 and either or both of the reference beams cancel as a result of the differencing operation at the coherent detector 36.

Figure 10:
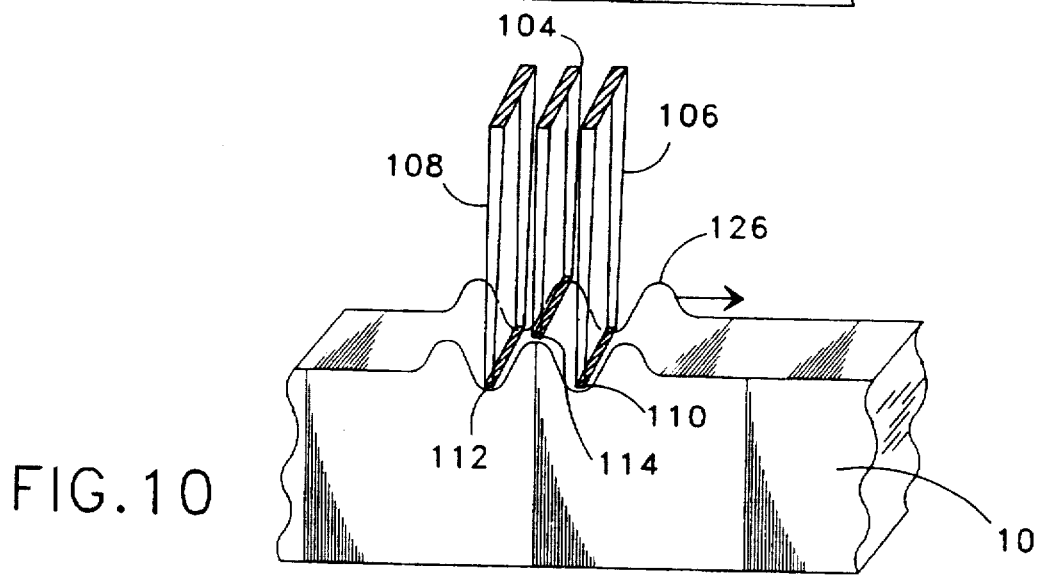
FIG. 10 is a perspective view of a surface wave with linear wavefronts propagating along a readout surface of a workpiece and of rectangular-shaped signal and reference beams used to measure the surface wave.

In situations where the wavefronts of the surface wave are linear (or approximately linear over the read out area), it is preferable to use a rectangular-shaped pattern for the signal and reference beams, as illustrated in FIG. 10. The thickness of the rectangular-shaped beams at the readout sites 112, 114 and 110 are preferably less than one-quarter of the surface wave 126 wavelength.

The systems illustrated in FIGS. 2 and 3 are preferred for optical reflections from a workpiece surface which are specular or only weakly depolarizing. However, many practical applications require optical readout from strongly depolarizing surfaces. The depolarizing case presents a number of problems to coherent detection and/or DPCM wavefront compensation. After reflection from a depolarizing workpiece surface, the reflected optical beams are not spatially homogeneous with respect to polarization and they are not polarization matched with each other. Thus, one polarization of each beam is rejected (reflected) by the polarizing beamsplitter (56 in FIGS. 2 and 3). In the event of complete depolarization, half the signal is lost at the polarizing beamsplitter. Furthermore, since the depolarization is typically spatially inhomogeneous, the reflected signal transmitted through the polarizing beamsplitter, and therefore the signal emerging from the DPCM compensator, will be temporally modulated with noise-like modulations as the depolarization properties of the probed areas change (for example, as a consequence of scanning).

Figure 11:
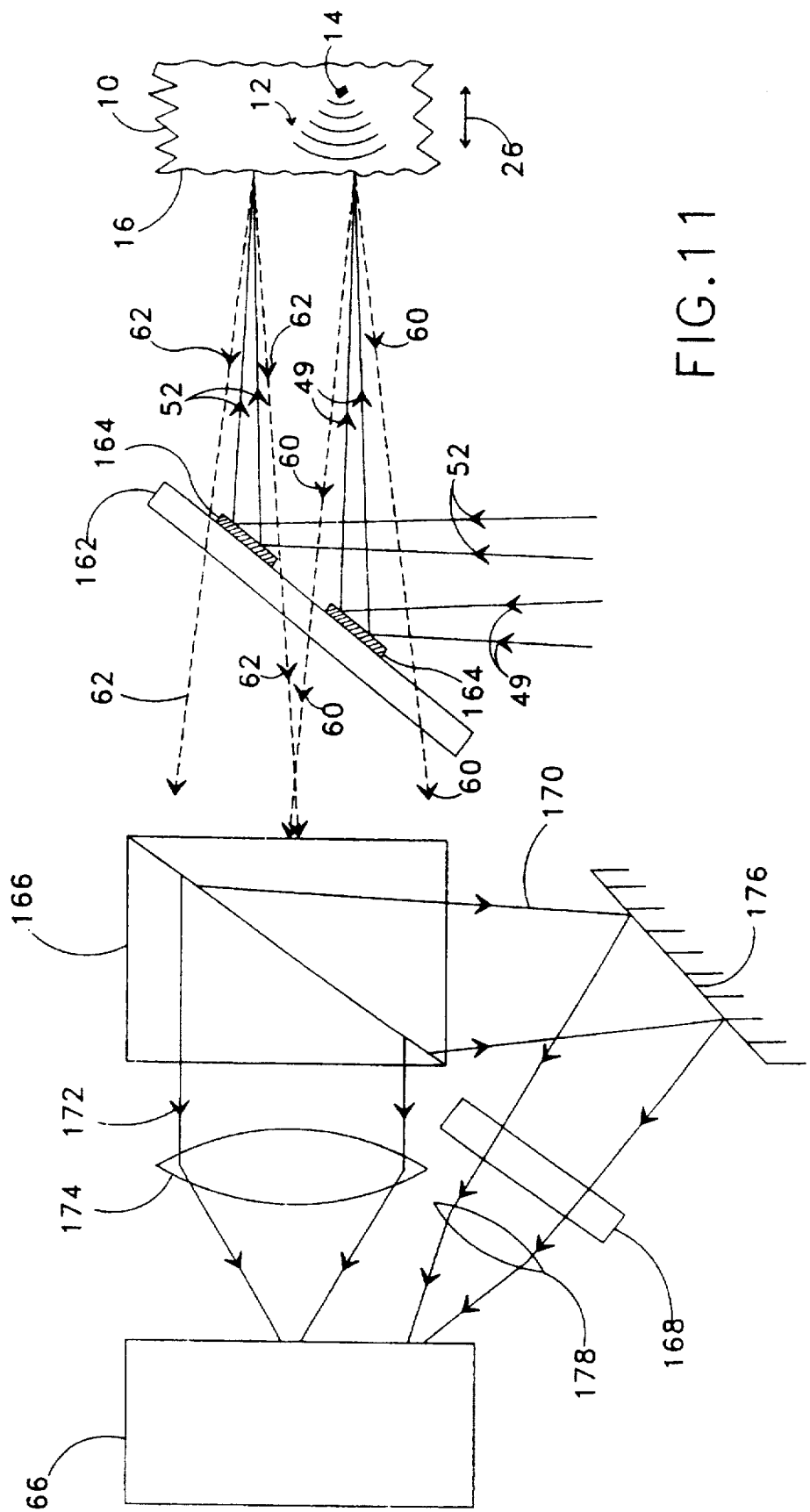
FIG. 11 is a schematic view of an alternate beam director embodiment for use in the systems of FIGS. 3 and 4.

As a result, applications involving depolarizing workpiece surfaces would preferably incorporate a polarization preserving mirror system which utilizes both polarization. FIG. 11 illustrates such a system. For illustration purposes, the mirror system of FIG. 11 is applied to the two beam system of FIG. 2, but it can also be applied to the three beam system of FIG. 3. Furthermore, the only elements reproduced from FIG. 2 are those needed to illustrate the modified mirror system.

The system's theory of operation is the same as that described for FIG. 2, with the following exceptions. Beams 49 and 52 are directed to the surface of the workpiece by a transparent optical flat 162 with reflecting regions 164. The reflecting regions are preferably fabricated by depositing aluminum onto the surface of the optical flat 162 and are preferably slightly larger than the projection of beams 49 and 52 at the optical flat 162. If the workpiece surface 16 is a highly scattering surface, the reflected beams 60 and 62 will be highly diverging and only a small portion of them will be blocked by the reflecting regions 164 when they pass through the optical flat 162. If the workpiece surface is not highly scattering, the workpiece 10 is oriented so that the workpiece surface 16 is tilted just enough to allow the reflected beams 60 and 62 to just miss the reflecting regions 164.

Since most DPCMs work most efficiently with one polarization component, a polarizing beamsplitter 166 and halfwave plate 168 system is utilized. For illustration, it is assumed that the photorefractive crystal 66 (DPCM) works most efficiently with P polarization. The reflected beams 60 and 62 enter the PBS 166 and are separated into their S-polarized components 170 and P-polarized components 172. The P-polarized components 172 are directed into the photorefractive crystal 66 by lens 174. The S-polarized components 170 are reflected by mirror 176 to the half-wave plate 168. The half-wave plate 168 rotates the polarization of the S-polarized components 170 by 90 degrees (so that they are now P-polarized) and the components are directed to the photorefractive crystal 66 by lens 178.

Thus, with the polarization preserving mirror system of FIG. 11, the spatial and amplitude variations of both polarization components of the signal and reference beams are compensated by the DPCM. Therefore, the reflected signal and reference beams 60 and 62 are not modulated by dynamic changes in their polarization state. In addition, since both polarization components are utilized, there is no loss of signal in the case of completely depolarizing workpiece surfaces. As explained above, the polarization preserving mirror system may also be incorporated into the three beam system of FIG. 3.

Numerous other variations and alternate embodiments will occur to those skilled in the art without departing from the spirit and scope of the invention. Accordingly, it is intended that the invention be limited only in terms of the appended claims.

We claim:

1. A self-referencing, non-contacting, laser-based ultrasonic wave receiver for detecting ultrasonic waves that vibrate a portion of a workpiece surface, comprising:

an optical beam generator for generating and directing signal and reference beams having a predetermined mutual frequency relationship to said surface, so that said signal and reference beams reflect off said surface with at least said signal beam reflecting of said vibrating surface portion and being phase modulated by said ultrasonic wave vibrations, and so that noise induced vibrations phase modulate said signal and reference beams, with said noise induced phase modulations on said signal and reference beams being in phase with respect to each other, a photorefractive crystal, a beam director for directing said reflected signal and reference beams to one side of said crystal, a second optical beam generator for generating and directing a compensator reference beam to another side of said crystal so that said compensator reference beam optically interferes with said reflected signal and reference beams in said crystal, thereby writing photorefractive refractive index gratings in said crystal that diffract said reflected signal and reference beams, substantially overlap and match their wavefronts, and remove said wavefront distortions without altering their respective optical phases, so that said signal and reference beams optically interfere and generate a beat frequency, with noise induced phase modulations that are common to said signal and reference beams substantially canceling as a result of destructive interference between them, and a signal monitor for extracting information about said ultrasonic waves from said beat frequency.

2. The receiver of claim 1, wherein said optical beam generator comprises:

a laser for generating an optical beam of a predetermined wavelength, a beam divider for dividing said optical beam into said signal and reference beams, a beam director for directing said signal and reference beams to said surface, and a beam focuser for focusing said beams onto said surface.

3. The receiver of claim 2, further comprising a beam sampler for extracting a detector reference beam from said optical beam.

4. The receiver of claim 3, wherein said signal monitor comprises:

a first coherent detector for detecting said beat frequency between said reflected signal and reference beams, a second detector for detecting said detector reference beam, a differential amplifier for receiving the output signals of said first and second detectors and for removing laser amplitude noise from said signals, an automatic gain control circuit for maintaining the power of said first and second detector output signals equal, and a processor for extracting information about said ultrasonic waves from said beat frequency.

5. The receiver of claim 4, further comprising a frequency shifter for shifting the frequency of at least one of said signal and reference beams so that said signal monitor can operate in a heterodyne mode.

6. The receiver of claim 1, wherein said optical beam generator directs said reference beam to a surface portion that is not being vibrated by said ultrasonic waves.

7. The receiver of claim 1, wherein said optical beam generator directs said signal and reference beams to said vibrating surface portion and spaces said beams on said surface portion so that said ultrasonic wave phase modulations on said signal and reference beams are 180 degrees out of phase with respect to each other, thereby constructively interfering when said beams optically interfere.

8. The receiver of claim 1, wherein said optical beam generator directs said signal and reference beams to said vibrating surface portion and spaces said beams on said surface portion so that said ultrasonic wave arrives at said signal and reference beams at different times.

9. A self-referencing, non-contacting, laser-based ultrasonic wave detector for detecting ultrasonic waves that vibrate a portion of a workpiece surface, comprising:

an optical beam generator for generating an optical beam, a beam divider for dividing said optical beam into a signal beam and at least two reference beams, a beam director for directing said signal and reference beams to said surface, so that said signal and reference beams reflect off said surface with at least said signal beam reflecting of said vibrating surface portion and being phase modulated by said ultrasonic wave vibrations, and so that noise induced vibrations phase modulate said signal and reference beams, with said noise induced phase modulations on said signal and reference beams being in phase with respect to each other, a wavefront compensator for removing wavefront distortions imparted onto said reflected signal and reference beams by said surface and for substantially overlapping and matching their wavefronts so that said beams optically interfere and generate a beat frequency, said noise induced phase modulations that are common to said beams substantially canceling out as a result of destructive interference between them, and a signal monitor for extracting information about said ultrasonic waves from said optical interference.

10. The receiver of claim 9, further comprising a beam focuser for focusing said signal and reference beams onto said surface so that said reference beams are spaced symmetrically about said signal beam.

11. The receiver of claim 10, wherein each of said symmetrically spaced reference beams illuminates a half-ring-shape d pattern on said surface.

12. The receiver of claim 10, wherein each of said signal and reference beams illuminates a rectangular-shaped pattern on said surface.

13. The receiver of claim 9, wherein said wavefront compensator comprises a double-pumped phase conjugate mirror system.

14. The receiver of claim 13, wherein said double-pumped phase conjugate mirror system comprises:
  a photorefractive crystal,
  a second beam director for directing said reflected signal and reference beams to said crystal, and
  a second optical beam generator for generating and directing a compensator reference beam to said crystal so that said compensator reference beam optically interferes with said reflected signal and reference beams in said crystal, thereby writing photorefractive refractive index gratings in said crystal that diffract said reflected signal and reference beams, substantially match their wavefronts and remove said wavefront distortions without altering their respective optical phases.

15. The receiver of claim 14, wherein said first and second beam directors are implemented with common components.

16. The receiver of claim 9, further comprising a beam sampler for extracting a detector reference beam from said optical beam.

17. The receiver of claim 16, wherein said signal monitor comprises:
  a first coherent detector for detecting said beat frequency between said reflected signal and reference beams,
  a second detector for detecting said detector reference beam,
  a differential amplifier for receiving the output signals of said first and second detectors and for removing laser amplitude noise from said signals,
  an automatic gain control circuit for maintaining the power of said first and second detector output signals equal, and
  a processor for extracting information about said ultrasonic waves from said beat frequency.

18. The receiver of claim 16, further comprising a frequency shifter for shifting the frequency at least one of said signal and reference beams so that said signal monitor can operate in a heterodyne mode.

19. The receiver of claim 10, wherein said beam director directs said reference beams to surface portions that are not being vibrated by said ultrasonic waves.

20. The receiver of claim 10, wherein said beam director directs said signal and reference beams to said vibrating surface portion and spaces said beams on said surface portion so that said ultrasonic wave phase modulations on said signal and reference beams are 180 degrees out of phase with respect to each other, thereby constructively interfering when said beams optically interfere.

21. The receiver of claim 10, wherein said beam director directs said signal and reference beams to said vibrating surface portion and spaces said beams on said surface portion so that said ultrasonic wave arrives at said signal and reference beams at different times.

22. A method of detecting ultrasonic waves in a workpiece, comprising the steps of:
  generating ultrasonic waves in said workpiece to vibrate a portion of a surface of said workpiece,
  phase modulating a signal beam with said vibrations by reflecting said signal beam off said vibrating surface portion,
  reflecting a reference beam having a predetermined phase relationship to said signal beam off said workpiece surface,
  directing said reflected signal and reference beams to one side of a photorefractive crystal,
  generating and directing a compensator reference beam to another side of said crystal so that said compensator reference beam optically interferes with said reflected signal and reference beams in said crystal, thereby writing photorefractive refractive index gratings in said crystal that diffract said reflected signal and reference beams, substantially overlap and match their wavefronts, and remove said wavefront distortions without altering their respective optical phases, and
  beating said signal and reference beams against each other to generate a beat frequency that contains information about said ultrasonic waves, and to cancel noise-induced phase modulations common to said beams.

23. The method of claim 22, wherein a detector reference beam having a predetermined phase relationship to said signal beam is generated.

24. The method of claim 23, wherein said ultrasonic wave information is extracted by:
  detecting said beat frequency with a first coherent detector,
  detecting said detector reference beam with a second detector,
  removing amplitude noise from the output signals of said first and second detectors with a differential amplifier,
  maintaining the power of said first and second detector output signals equal with an automatic gain control circuit,
  extracting said ultrasonic wave information from said beat frequency with a processor.

25. The method of claim 24, wherein said signal beam is frequency shifted so that said detector and processor can operate in a heterodyne mode.

26. The method of claim 22, wherein one signal beam and at least two reference beams are reflected from said surface.

27. The method of claim 26, wherein said reference beams are reflected from portions on said surface that are symmetrically spaced about said signal beam.

28. The method of claim 27, wherein each of said reference beams illuminates a half-ring-shaped pattern on said surface.

29. The method of claim 27, wherein each of said signal and reference beams illuminates a rectangular-shaped pattern on said surface.

30. The method of claim 22, wherein said reference beam reflects off a surface portion that is not being vibrated by said ultrasonic waves.

31. The method of claim 22, wherein said reference beam reflects off said vibrating surface portion so that said ultrasonic wave phase modulations on said reference beam are 180 degrees out of phase with said ultrasonic wave phase modulations on said signal beam, thereby constructively interfering when said beams are beat against each other.

32. The method of claim 22, wherein said reference beam reflects off said vibrating surface portion so that said ultrasonic waves arrive at said reference beam at a different time than they arrive at said signal beam.

33. A method of detecting ultrasonic waves in a workpiece, comprising the steps of:
  generating ultrasonic waves in said workpiece to vibrate a portion of a surface of said workpiece,
  phase modulating a signal beam with said vibrations by reflecting said signal beam off said vibrating surface portion, reflecting at least two reference beams having predetermined phase relationships to said signal beam off said workpiece surface, removing wavefront distortions from said signal and reference beams, and beating said signal and reference beams against each other to generate a beat frequency that contains information about said ultrasonic waves, and to cancel noise-induced phase modulations common to said beams.

34. The method of claim 33, wherein said reference beams are reflected from portions on said surface that are symmetrically spaced about said signal beam.

35. The method of claim 34, wherein each of said reference beams illuminates a half-ring-shaped pattern on said surface.

36. The method of claim 34, wherein each of said signal and reference beams illuminates a rectangular-shaped pattern on said surface.

* * * * *